United States Patent [19]

Hargreaves et al.

[11] Patent Number: 4,493,835
[45] Date of Patent: Jan. 15, 1985

[54] 1,3,4-THIADIAZINES

[75] Inventors: Rodney B. Hargreaves, Poynton; Bernard J. McLoughlin, Macclesfield, both of England

[73] Assignee: Imperial Chemical Industries PLC, London, England

[21] Appl. No.: 436,802

[22] Filed: Oct. 26, 1982

[30] Foreign Application Priority Data

Nov. 12, 1981 [GB] United Kingdom ............... 8134176

[51] Int. Cl.³ ................. C07D 285/16; A61K 31/54
[52] U.S. Cl. ............................................. 424/246; 544/8
[58] Field of Search ......................... 544/8; 424/246

[56] References Cited

U.S. PATENT DOCUMENTS

| | | | |
|---|---|---|---|
| 3,377,345 | 4/1968 | Trepanier | 260/244 |
| 3,514,455 | 5/1970 | Takamizawa et al. | 260/243 |
| 3,946,010 | 3/1976 | Wada et al. | 260/248 X |
| 4,097,425 | 6/1978 | Niznik | 260/2.5 |
| 4,105,848 | 8/1978 | Ehlinger | 544/68 |
| 4,158,094 | 6/1979 | Niznik | 544/68 |
| 4,423,045 | 12/1983 | Brown et al. | 544/8 |

OTHER PUBLICATIONS

Lempert-Sreter et al., Chem Abstr., vol. 88, 170106 (1978).
Holmberg, Chemical Abstracts, vol. 50, 7816f (1956).
Pyridazines, VI. Some 6-Substituted 3(2H) pyridazinones (1), Edgar A. Steck, R. Pauline Brundage, and Lynn T. Fletcher, J. Heterocyclic Chem., vol. 11, pp. 755-761, Oct. 1974.
Journal of Pharmaceutical Science, "New compounds: 4 Substituted 5,6-Dihydro-2-o-hydroxyphenyl-4H-1,2,4-oxadiazine-5-ones, Potential Psychopharmacological Drugs", Susan M. Sicardi, Samuel Lamdan, and Carlos H. Gaozza.
Jour. of Heterocyclic Chemistry, "Intramolecular Cyclization of N'Chloroacetlslicylhydrazide" C. H. Gaozza and S. Lamdan, Aug. 1970, pp. 927-930, vol. 7.
"Synthesis and Structure of Dihydro-1,2,4-triazin-6(1H)ones(1)", Alfredo Camparini, Angela Maria Celli and Fabio Ponticelli, vol. 15, Dec. 1978, Jour. of Heterocyclic Chemistry, pp. 1271-1276.

Primary Examiner—John M. Ford
Attorney, Agent, or Firm—Cushman, Darby & Cushman

[57] ABSTRACT

Heterocyclic compounds of the formula:

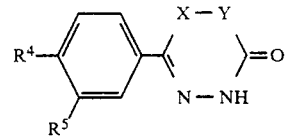

wherein either X is $-CR^1R^2-$ and Y is $-O-$, $-S-$ or $-NHR^3-$, wherein $R^1$, $R^2$ and $R^3$, which may be the same or different, each is hydrogen or alkyl of up to 4 carbon atoms;

or X is $-O-$, $-S-$ or $-NH-$ and Y is $-CR^1R^2-$ wherein $R^1$ and $R^2$ have the meanings stated above; wherein $R^4$ and $R^5$, which may be the same or different, each is hydrogen (but provided that $R^4$ and $R^5$ are not both hydrogen), or each is a group defined in claim 1 which is readily convertible into a carboxy group; processes for their manufacture; and pharmaceutical compositions containing them. The compounds possess cardiotonic and/or antihypertensive activity.

8 Claims, No Drawings

1,3,4-THIADIAZINES

This invention relates to new heterocyclic compounds, some of which possess cardiotonic properties, some of which possess antihypertensive properties and some of which possess both said properties.

Many 6-aryl-dihydropyridazin-3-one derivatives are known which possess pharmaceutical properties affecting the cardiovascular system. These are described, for example, in the Journal of Medicinal Chemistry, 1974, 17, 273-286 and in the Journal of Heterocyclic Chemistry, 1974, 11, 755-761, and there is much related patent literature.

When an additional hetero-atom is inserted into the pyridazine nucleus, most of the simple structures have been described in the academic chemical literature. Thus, for example:

2-phenyl-4H,6H-1,3,4-thiadiazin-5-one and its 6-methylanalogue are known from Chemical Abstracts, 1948, 42 5919 and 1956, 50, 7817;

5-phenyl-3H,6H-1,3,4-thiadiazin-2-one and its 6-methyl analogue are known from Leibig's Annalen der Chemie, 1977, 791 and from this article are also known the corresponding p-bromophenyl and 4-biphenylyl analogues;

2-phenyl-4H,6H-1,3,4-oxadiazin-5-one is known from Receuil des Tavaux chimiques des Pays Bas, 1929, 48, 417 and o-hydroxyphenyl analogues thereof are known from J. Heterocyclic Chemistry, 1970, 7; 927;

3-phenyl-4,5-dihydro-5-methyl-1H-1,2,4-triazin-6-one is known from J. Heterocyclic Chemistry, 1978, 15, 1271; 6-phenyl-4,5-dihydro-2H-1,2,4-triazin-3-one and its 4-methyl analogue are known from Chemical Abstracts, 1970, 73, 35334.

From the patent literature 5-phenyl-3H,6H-1,3,4-oxadiazin-2-one and the corresponding 4-bromophenyl and 2-naphthyl analogues are known as blowing agents in the plastics industry, from U.S. Pat. Nos. 4,097,425, 4,105,848 and 4,158,094.

None of the abovementioned references discloses any pharmacological utility for any of the compounds described. The only references to pharmacological activity in this kind of compound of which applicants are aware appear in U.S. Pat. No. 3,514,455, which describes various 4,6-disubstituted-2-phenyl-4H,6H-1,3,4-thiadiazin-5-one derivatives which are claimed to possess antipyretic, analgesic, anti-inflammatory and antiedema activities, and in U.S. Pat. No. 3,946,010, which describes various 3-o-aminophenyl-4,5-dihydro-1H-1,2,4-triazine-6-one derivatives which are claimed to possess anti-inflammatory activity.

A compound of considerable interest at present as a cardiotonic agent is a pyridone derivative known by the name AMRINONE, which has the structure:

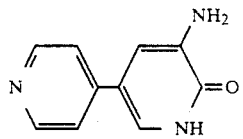

We have now found that various phenylthiadiazinone, oxadiazinone or triazinone derivatives which bear a substituent in the 3- or 4-position of the phenyl nucleus possess valuable cardiotonic and/or antihypertensive properties.

According to the invention there is provided a heterocyclic compound of the formula:

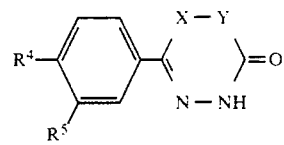

wherein either X is —CR$^1$R$^2$— and Y is —O—, —S— or —NR$^3$—, werein R$^1$, R$^2$ and R$^3$, which may be the same or different, each is hydrogen or alkyl of up to 4 carbon atoms;

or X is —O—, —S— or —NH— and Y is —CR$^1$R$^2$— wherein R$^1$ and R$^2$ have the meanings stated above; wherein R$^4$ and R$^5$, which may be the same or different, each is hydrogen (but provided that R$^4$ and R$^5$ are not both hydrogen), or each has the formula:

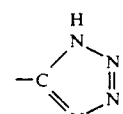

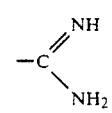

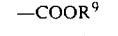

wherein R$^6$ and R$^7$, which may be the same or different, each is hydrogen, alkyl of up to 4 carbon atoms or arylalkyl of up to 10 carbon atoms; and wherein R$^8$ and R$^9$, which may be the same or different, each has the formula:

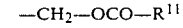

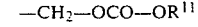

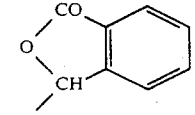

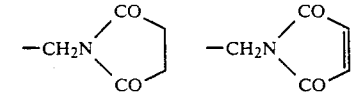

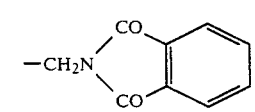

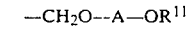

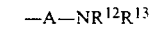

—A—COOR$^{12}$

—A—CONR$^{12}$R$^{13}$ wherein m is an integer from 2 to 4, A is alkylene of from 1 to 4 carbon atoms, R$^{11}$ is alkyl of up to 4 carbon atoms and R$^{12}$ and R$^{13}$, which may be the same or different, each is hydrogen or alkyl of up to 4 carbon atoms; or a salt thereof where appropriate.

A suitable value for R$^1$, R$^2$, R$^3$, R$^6$, R$^7$, R$^{11}$, R$^{12}$ or R$^{13}$ when it is alkyl is, for example, methyl, ethyl or t-butyl.

A suitable value for R$^6$ or R$^7$ when it is arylalkyl is, for example, benzyl.

A suitable value for A is, for example, methylene, ethylene or ethylidene.

An appropriate salt is an acid-addition salt, for example a hydrochloride, hydrobromide, acetate, oxalate, tartrate or citrate, of a compound wherein R$^4$ and/or R$^5$ is a basic group, for example a group of the formula —A—NR$^{12}$R$^{13}$ wherein A, R$^{12}$ and R$^{13}$ have the meanings stated above; or a base-addition salt, for example a sodium, potassium, ammonium or benzylamine salt, of an acid compound wherein R$^4$ and/or R$^5$ has the formula —A—COOR$^{12}$ wherein A has the meaning stated above and R$^{12}$ is hydrogen.

A preferred heterocyclic compound of the invention has the formula:

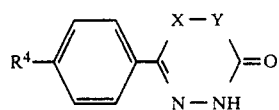

wherein either X is —CH$_2$ and Y is —NH; or X is —O— or —S— and Y is —CH$_2$—; and R$^4$ has the formula:

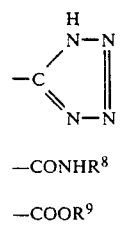

—CONHR$^8$

—COOR$^9$ wherein R$^8$ and R$^9$, which may be the same or different, each has the formula:

—CH$_2$OCOR$^{11}$

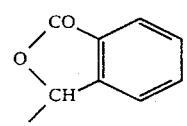

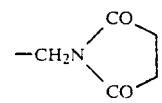

—(CH$_2$)$_m$—OH

—(CH$_2$)$_m$—NR$^{12}$R$^{13}$

—CH$_2$—O—A—OR$^{11}$

—A—COOR$^{12}$

—ACON$^{12}$R$^{13}$ wherein m is an integer from 2 to 4, especially 2, A is alkylene of from 1 to 3 carbon atoms, especially —CH$_2$—, —CH(CH$_3$)—, —CH$_2$CH$_2$— or —(CH$_2$)$_3$, R$^{11}$ is alkyl of up to 4 carbon atoms, especially methyl, ethyl or t-butyl, and R$^{12}$ and R$^{13}$, which may be the same or different, each is hydrogen or alkyl of up to 4 carbon atoms, especially —OR$^{12}$ having hydrogen, methyl or ethyl for R$^{12}$ and —NR$^{12}$R$^{13}$ hving R$^{12}$ and R$^{13}$ either both hydrogen, or both methyl or both ethyl.

Preferably X is —S— and Y is —CH$_2$.

Specific heterocyclic compounds of the invention are hereinafter described in the Examples. Of these, preferred compounds are 3-ethoxycarbonylpropyl, 1-ethoxycarbonylethyl, 1-N N-diethylcarbamoylethyl and pivalyloxymethyl p-(5-6-dihydro-5-oxo-4H-1,3,4-thiazin-2-yl)benzoate.

A preferred process for the manufacture of a heterocyclic compound of the invention comprises the modification of the corresponding heterocyclic compound wherein R$^4$ and/or R$^5$ is cyano or carboxy (which compounds are described in our European Specification No. 52442), or of an activated derivative thereof, by conventional means. Thus, an acid wherein R$^4$ and/or R$^5$ is carboxy, or an activated derivative thereof, may be reacted with hydrazine, or with a hydroxylamine of the formula HNR$^6$—OR$^7$, or with an amine of the formula HNR$^7$R$^8$, or with an alcohol of the formula HOR$^9$, wherein R$^6$, R$^7$, R$^8$ and R$^9$ have the meanings stated above, or with an activated derivative thereof; and a compound wherein R$^4$ and/or R$^5$ is cyano may be converted to the corresponding compound wherein R$^4$ and/or R$^5$ is amidino or 5-tetrazolyl by conventional means.

A particularly preferred process for the manufacture of a compound of the formula:

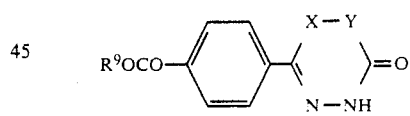

wherein R$^9$, X and Y have the meanings stated above, comprises the reaction of an acid wherein R$^4$ is carboxy and R$^5$ is hydrogen with a compound of the formula R$^9$—Cl wherein R$^9$ has the meaning stated above.

An alternative process for the manufacture of a compound of the invention wherein X is oxygen or sulphur and Y is —CR$^1$R$^2$— comprises the reaction of a hydrazide or thiohydrazide of the formula:

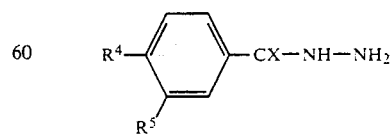

wherein R$^4$ and R$^5$ have the meanings stated above and X is sulphur or oxygen, with an acid of the formula:

Hal—CR$^1$R$^2$—COOH wherein $R^1$ and $R^2$ have the meanings stated above and wherein Hal is a halogen atom, for example the chlorine or bromine atom, or with a reactive derivative thereof.

When X is sulphur the acid is preferably used directly, and the reaction may be carried out in aqueous solution, in the presence of a base, for example, sodium hydroxide, at laboratory temperature.

When X is oxygen the acid is preferably used as a reactive derivative thereof, for example the acyl halide, and the reaction carried out in two stages. The benzoylhydrazine may be reacted with the acyl halide in an inert solvent, for example toluene, in the presence of a base, for example potassium carbonate. The diacyl hydrazine thus obtained may then be reacted with a base, for example sodium hydride, in a dipolar aprotic solvent, for example dimethylformamide, or with an alkali metal carbonate in acetone, and the reaction may be carried out at an elevated temperature, for example at about 100° C.

An alternative process for the manufacture of a compound of the invention wherein X is $-CR^1R^2-$ and Y is sulphur comprises the reaction of a phenacyl halide of the formula:

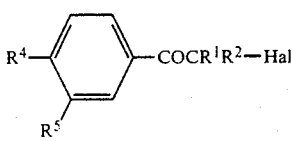

wheren $R^1$, $R^2$, $R^4$, $R^5$ and Hal have the meanings stated above, with a thiocarbazate of the formula:

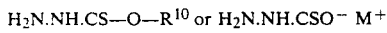

wherein $R^{10}$ is alkyl of up to 4 carbon atoms, for example methyl or ethyl, and wherein $M^+$ is an alkali metal or ammonium ion.

The reaction may be carried out in an organic diluent or solvent, for example acetonitrile or ethanol, at an elevated temperature, for example at the boiling point of the diluent or solvent.

An alternative process for the manufacture of a compound of the invention wherein X is $-CR^1R^2-$ and Y is oxygen comprises the cyclisation of a compound of the formula:

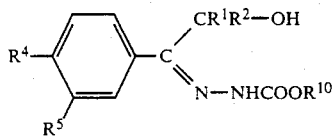

wherein $R^1$, $R^2$, $R^4$, $R^5$ and $R^{10}$ have the meanings stated above. The cyclisation may be carried out in the presence of a base, for example sodium ethoxide, in a diluent or solvent, for example ethanol, at laboratory temperature.

The starting material for the last-mentioned reaction may be obtained by the reaction of a compound of the formula:

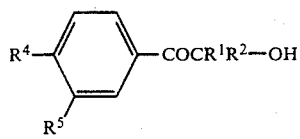

wherein $R^1$, $R^2$, $R^4$ and $R^5$ have the meanings stated above, with an alkyl carbazate of the formula:

wherein $R^{10}$ has the meaning stated above.

An alternative process for the manufacture of a compound of the invention wherein X is $-NH-$ and Y is $-CR^1R^2-$ comprises the reaction of a compound of the formula:

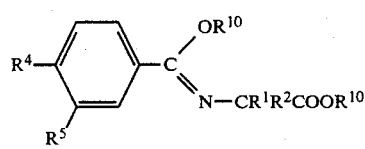

wherein $R^1$, $R^2$, $R^4$, $R^5$ and $R^{10}$ have the meanings stated above (the two $R^{10}$ substituents being the same or different alkyl radicals of up to 4 carbon atoms), with hydrazine.

The reaction may be carried out in a diluent or solvent, for example ethanol, at a temperature up to the boiling point of the diluent or solvent.

The starting material for the last-mentioned reaction may be obtained either by the reaction of a compound of the formula:

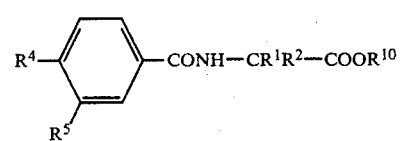

wherein $R^1$, $R^2$, $R^4$, $R^5$ and $R^{10}$ have the meanings stated above, with an oxonium trifluoroborate of the formula $(R^{10})_3OBF_4$, wherein $R^{10}$ has the meaning stated above, or by the reaction of a compound of the formula:

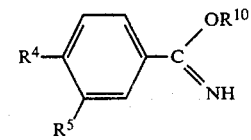

wherein $R^4$, $R^5$ and $R^{10}$ have the meanings stated above, with a glycine ester of the formula $H_2NR^1R^2COOR^{10}$, wherein $R^1$, $R^2$, and $R^{10}$ have the meanings stated above.

An alternative process for the manufacture of a compound of the invention wherein X is $-CR^1R^2-$ and Y is $-NR^3-$ comprises the reaction of a compound of the formula:

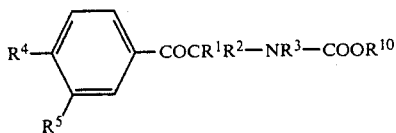

wherein $R^1$, $R^2$, $R^3$, $R^4$ $R^5$ and $R^{10}$ have the meanings stated above, with hydrazine.

The reaction may be carried out in a diluent or solvent, for example ethanol, at a temperature up to the boiling point of the diluent or solvent.

The starting material for the last-mentioned process may be obtained by the reaction of a compound of the formula:

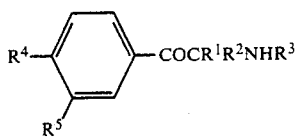

wherein $R^1$, $R^2$, $R^3$, $R^4$ and $R^5$ have the meanings stated above, with a chloroformate of the formula $R^{10}OCOCl$, wherein $R^{10}$ has the meaning stated above.

A compound of the invention wherein $R^3$ is alkyl may be obtained by the alkylation of the correspondinging compound wherein $R^3$ is hydrogen.

As stated above, some of the heterocyclic compounds of the invention possess cardiotonic activity. This may be demonstrated by their ability to increase the rate of change of aortic blood pressure in the anaesthetised cat. At a dose of the compound which produces an effective increase in said rate of change, that is, greater than a 25% increase, no symptom of toxicity is apparent.

As stated above, some of the heterocyclic compounds of the invention possess antihypertensive activity, as demonstrated by their ability to decrease the blood pressure of a normotensive cat or of a spontaneously hypertensive rat. The anti-hypertensive activity may also be demonstrated by the vasodilation effect produced by the heterocyclic compounds of the invention as shown by their ability to reduce spontaneous contraction in a rat portal vein preparation.

The heterocyclic compound of the invention may be administered to warm-blooded animals, including man, in the form of a pharmaceutical composition comprising as active ingredient at least one heterocyclic compound of the invention in association with a pharmaceutically acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the heterocyclic compound of the invention, one or more drugs selected from sedatives, for example phenobarbitone, meprobamate, chlorpromazine and benzodiazepine sedative drugs, for example chlordiazepoxide and diazepam; vasodilators, for example hydralazine, glyceryl trinitrate, pentaerythritol tetranitrate and isosorbide dinitrate; diuretics, for example chlorothiazide, hydrochlorothiazide, amiloride, bendrofluazide or chlorthalidone; β-adrenergic blocking agents, for example propranolol or atenolol; cardiac membrane stabilising agents, for example quinidine; agents used in the treatment of Parkinson's disease and other tremors, for example benzhexol; and cardiotonic agents, for example digitalis preparations.

When used for the treatment of acute or chronic heart failure or or hypertension in man, it is expected that the heterocyclic compound would be given to man at a total oral dose of between 100 mg. and 2000 mg. daily, at doses of 6–8 hourly intervals, or at an intravenous dose of between 5 mg. and 100 mg.

Preferred oral dosage forms are tablets or capsules containing between 50 and 500 mg., and preferably 100 mg. or 500 mg., of active ingredient. Preferred intravenous dosage forms are sterile aqueous solutions of the heterocyclic compound containing between 0.05% and 1% w/w of active ingredient, and more particularly containing 0.1% w/v of active ingredient.

The invention is illustrated but not limited by the following Examples:

EXAMPLE 1

Chloromethyl pivalate (0.908 g.) was added dropwise during 3 minutes to a stirred suspension of p-(5,6-dihydro-5-oxo-4H-1,3,4-thiadiazin-2-yl)benzoic acid (0.28 g.) and potassium carbonate (0.174 g.) in dimethylformamide (12 ml.) which had been stirred at laboratory temperature for 30 minutes. The mixture was stirred for a further 2 hours, kept at laboratory temperature for 18 hours and then poured into saturated aqueous sodium chloride solution (100 ml.). The mixture was extracted twice with ethyl acetate (30 ml. each time) and the combined extracts were dried over magnesium sulphate and evaporated to dryness. The residue was crystallised from a mixture of ethyl acetate and petroleum ether (b.p. 60°–80°) and there was thus obtained pivalyloxymethyl p-(5,6-dihydro-5-oxo-4H-1,3,4-thiadiazin-2-yl)benzoate, m.p. 133°–134.5° C.

EXAMPLE 2

A mixture of p-(2,3,4,5-tetrahydro-3-oxotriazin-6-yl)benzoic acid (1.0 g.) and thionyl chloride (150 ml.) was heated under reflux for 5 hours and then evaporated to dryness under reduced pressure. The residue was cooled to 0° C. and a solution of ethyl glycinate hydrochloride (7.0 g.) and sodium acetate (8.2 g.) in water (50 ml.), also cooled to 0° C., was added. The mixture was allowed to warm up to laboratory temperature, stirred at that temperature for 5 minutes, stirred and heated at 50° C. for 10 minutes, and ethanol (5 ml.) was added. The mixture was filtered and the solid residue was washed with water and then crystallised from ethanol. There was thus obtained ethyl [p-(2,3,4,5-tetrahyro-3-oxotriazin-6-yl)benzamido]acetate, m.p. 198°–200° C. (with decomposition).

The process described above was repeated using β-aminoethanol or β-dimethylaminoethylamine in place of ethyl glycinate hydrochloride, and there were thus obtained, respectively, N-(β-hydroxyethyl)-p-(2,3,4,5-tetrahydro-3-oxotriazine-6-yl)benzamide, m.p. 288°–290° C., and N-(β-dimethylaminoethyl)-p-(2,3,4,5-tetrahydro-3-oxotriazin-6-yl)benzamide, m.p. 227°–23-°C. (both of which were crystallised from methanol.

EXAMPLE 3

A mixture of ethyl [p-(2,3,4,5-tetrahydro-3-oxotriazin-6-yl)benzamido]acetate (Example 2; 0.2 g.), aqueous 2N-sodium hydroxide solution (5 ml.) and methanol (5 ml.) was heated at 50° C. for 15 minutes, cooled, acidified to pH 2 with aqueous 2N hydrochloric acid and filtered. The solid residue was crystallised from methanol and there was thus obtained p-(2,3,4,5-tetrahydro-3-oxotriazin-6-yl)benzamidoacetic acid, m.p. 270°–271° C. (with decomposition).

EXAMPLE 4

Aqueous ammonium hydroxide solution (specific gravity 0.88; 2 ml.) was added to a solution of ethyl [p-(2,3,4,5-tetrahydro-3-oxotriazin-6-yl)benzamido]acetate (0.4 g.) in ethanol (10 ml.) and the mixture was heated under reflux for 5 minutes and then evaporated to dryness under reduced pressure. The residue was crystallised from methanol and there was thus obtained p-(2,3,4,5-tetrahydro-3-oxotriazin-6-yl)benzamidoacetamide, m.p. 252° C. (with decomposition).

EXAMPLE 5

A mixture of 6-p-cyanophenyl-4,5-dihydro-1,2,4-triazin-3(2H)-one (1.0 g.), ammonium chloride (0.27 g.), sodium azide (0.325 g.) and dimethylformamide (50 ml.) was heated at 90° C. for 3 days, cooled and evaporated to dryness under reduced pressure. Water (50 ml.) was added, the mixture was filtered and the solid residue was crystallised from methanol and then from a mixture of methanol and dimethylformamide. There was thus obtained 4,5-dihydro-6-p-(tetrazol-5-yl)phenyl-1,2,4-triazin-3-(2H)-one.

EXAMPLE 6

The process described in Example 1 was repeated except that the appropriate chloro- or bromoalkyl ester was used in place of chloromethyl pivalate, and that the mixture was stirred for 18 hours. There were thus obtained the compounds described in the following table (all of which were crystallised from the same solvent mixture as in Example 1):

| $R^9$ | m.p. (°C.) |
|---|---|
| $C_2H_5O$—$COCH_2$— | 155–157+ |
| $CH_3OCH_2CH_2OCH_2$— | 97–100 |
| $C_2H_5OCO(CH_2)_3$— | 89–92+ |
| $C_2H_5OCOCH(CH_3)$— | 181–184+ |
| $(C_2H_5)_2NCOCH_2$— | 184–187 |
| $(C_2H_5)_2NCOCH(CH_3)$— | 178–180+ |
| Succinimido-$CH_2$— | 223–225+ |
| Phthalidyl- | 245* |

*Mixture stirred for 64 hours instead of 18 hours.
+Bromoalkyl ester used.

EXAMPLE 7

The process described in Example 1 was repeated except that the appropriate benzoic acid was used as starting material in place of p-(5,6-dihydro-5-oxo-4H-1,3,4-thiadiazin-2-yl)benzoic acid. There were thus obtained: pivalyloxymethyl p-(5,6-dihydro-5-oxo-4H-1,3,4-oxadiazin-2-yl)benzoate, m.p. 157°–158° C. (reaction mixture worked up after stirring for 2 hours and not allowed to stand for 18 hours); and pivalyloxymethyl p-(2,3,4,5-tetrahydro-3-oxo-1,2,4-triazin-6-yl)benzoate, m.p. 195°–198° C. (reaction mixture stirred for 18 hours).

What we claim is:

1. A heterocyclic compound of the formula

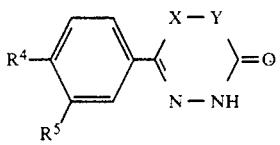

wherein X is —S— and Y is —$CR^1R^2$— wherein $R^1$ and $R^2$, which may be the same or different, each is hydrogen or alkyl of up to 4 carbon atoms; wherein $R^4$ and $R^5$, which may be the same or different, each is hydrogen (but provided that $R^4$ and $R^5$ are not both hydrogen), or each has the formula:

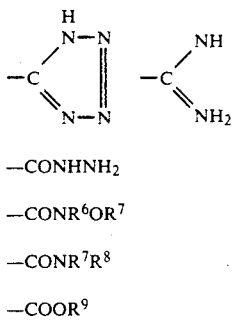

—$CONHNH_2$

—$CONR^6OR^7$

—$CONR^7R^8$

—$COOR^9$ wherein $R^6$ and $R^7$, which may be the same or different, each is hydrogen, alkyl of up to 4 carbon atoms or arylalkyl of up to 10 carbon atoms; and wherein $R^8$ and $R^9$, which may be the same or different, each has the formula:

—$CH_2$—OCO—$R^{11}$

—$CH_2$—OCO—$OR^{11}$

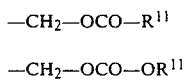

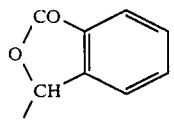

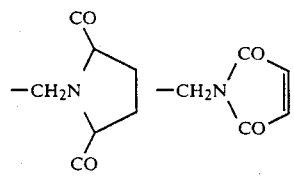

—$(CH_2)_mOH$

—$CH_2O$—A—$OR^{11}$

—A—$NR^{12}R^{13}$

—A—$COOR^{12}$

—A—$CONR^{12}R^{13}$ wherein m is an integer from 2 to 4, A is alkylene of from 1 to 4 carbon atoms, $R^{11}$ is alkyl of up to 4 carbon atoms and $R^{12}$ and $R^{13}$, which may be the same or different, each is hydrogen or alkyl of up to 4 carbon atoms; or a salt thereof where appropriate.

2. A heterocyclic compound of the formula:

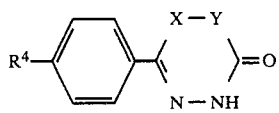

wherein X is —S— and Y is —CH$_2$—; and $R^4$ has the formula:

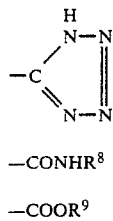

—CONHR$^8$

—COOR$^9$ wherein $R^8$ and $R^9$, which may be the same or different, ech has the formula

—CH$_2$OCOR$^{11}$

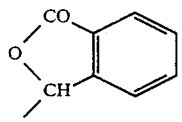

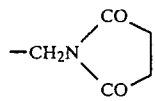

—(CH$_2$)$_m$—OH

—(CH$_2$)$_m$—NR$^{12}$R$^{13}$

—CH$_2$—O—A—OR$^{11}$

—A—COOR$^{12}$

—ACON$^{12}$R$^{13}$ wherein m is an integer from 2 to 4, A is alkylene of from 1 to 3 carbon atoms, $R^{11}$ is alkyl of up to 4 carbon atoms and $R^{12}$ and $R^{13}$, which may be the same or different, each is hydrogen or alkyl of up to 4 carbon atoms.

3. A heterocyclic compound as claimed in claim 2 wherein m is 2, A is —CH$_2$, —CH(CH$_3$)—, —CH$_2$CH$_2$— or —(CH$_2$)$_3$—, $R^{11}$ is methyl, ethyl or t-butyl, $R^{12}$, when part of —OR$^{12}$, is hydrogen, methyl or ethyl and $R^{12}$ and $R^{13}$, when part of —NR$^{12}$R$^{13}$, are both hydrogen, both methyl or both ethyl.

4. The compound 3-ethoxycarbonylpropyl, 1-ethoxycarbonylethyl, 1-N,N-diethylcarbamoylethyl or pivalyloxymethyl p-(5,6-dihydro-5-oxo-4-H-1,3,4-thidiazin-2-yl)benzoate.

5. A pharmaceutical composition having cardiotonic or antihypertensive activity comprising as active ingredient at least one heterocyclic compound, claimed in claim 1, in association with a pharmaceutically-acceptable diluent or carrier therefor.

6. A composition as claimed in claim 5 which contains, in addition to the heterocyclic compound, one or more drugs selected from sedatives, vasodilators, diuretics, cardiac membrane stabilising agents, agents used in the treatment of Parkinson's disease and other tremors, and cardiotonic agents.

7. A method for the treatment of acute or chronic heart failure in a warm-blooded animal in need of such treatment which comprises administering to said animal an effective amount of a heterocyclic compound claimed in claim 1.

8. The compound pivalyloxymethyl p-(5,6-dihydro-5-oxo-4H-1,3,4-thiadiazin-2-yl)benzoate.

* * * * *